(12) United States Patent
Breibart

(10) Patent No.: US 10,285,839 B2
(45) Date of Patent: May 14, 2019

(54) STABILIZATION ENHANCEMENT EXERCISE DEVICE AND ASSOCIATED METHOD

(71) Applicant: PHYSICALMIND, INC., New York, NY (US)

(72) Inventor: Joan Breibart, New York, NY (US)

(73) Assignee: PHYSICALMIND, INC., New York, NY (US)

( * ) Notice: Subject to any disclaimer, the term of this patent is extended or adjusted under 35 U.S.C. 154(b) by 126 days.

(21) Appl. No.: 15/287,352

(22) Filed: Oct. 6, 2016

(65) Prior Publication Data

US 2017/0100638 A1     Apr. 13, 2017

Related U.S. Application Data

(60) Provisional application No. 62/239,119, filed on Oct. 8, 2015.

(51) Int. Cl.
*A61F 5/00* (2006.01)
*A63B 21/00* (2006.01)
(Continued)

(52) U.S. Cl.
CPC ................. *A61F 5/01* (2013.01); *A61F 5/00* (2013.01); *A63B 21/028* (2013.01);
(Continued)

(58) Field of Classification Search
CPC .......... A61F 5/01; A61F 5/00; A63B 21/4007; A63B 21/4033; A63B 21/4013; A63B 21/028; A63B 69/0057; A63B 2225/09; A63B 2209/10; A63B 2208/0228; A63B 2208/0214; A63B 2208/0204; A63B 2022/0092; A63B 23/0482; A63B 23/0405; A63B 23/03525; A63B 23/03508; A63B 23/0238; A63B 23/0216; A63B 21/4034; A63B 21/00047; A63B 69/0059; A63B 2225/62; A63B 2208/0252; A63B 23/10; A63B 21/4015; A63B 21/4019; A63B 21/4021; A63B 21/4035; A63B 21/4039;
(Continued)

(56) References Cited

U.S. PATENT DOCUMENTS 1,801,769 A * 4/1931 Gartner .................. A63B 23/10
                                                                482/79
2,013,481 A * 9/1935 Stonehill ................ A47C 7/383
                                                                297/230.13
(Continued)

*Primary Examiner* — Sundhara M Ganesan
*Assistant Examiner* — Shila Jalalzadeh Abyaneh
(74) *Attorney, Agent, or Firm* — R. Neil Sudol; Henry D. Coleman

(57) ABSTRACT

A device for facilitating or enhancing torso and pelvis stability exercises includes two elongate semi-cylindrical resiliently compressible members so coupled to one another as to maintain a mutually parallel configuration, the resiliently compressible members each having a planar side and a cylindrically arcuate side, the planar sides being co-planar with one another. A user attachment component holds the resiliently compressible members to the user with the planar sides in contact with the user in one use configuration and so that the arcuate sides are in contact with the user in an alternate use configuration.

1 Claim, 6 Drawing Sheets

(51) Int. Cl.
*A61F 5/01* (2006.01)
*A63B 21/02* (2006.01)
*A63B 23/035* (2006.01)
*A63B 23/04* (2006.01)
*A63B 23/10* (2006.01)
*A63B 69/00* (2006.01)
*A63B 23/02* (2006.01)
*A63B 22/00* (2006.01)

(52) U.S. Cl.
CPC ...... *A63B 21/4007* (2015.10); *A63B 21/4013* (2015.10); *A63B 21/4033* (2015.10); *A63B 69/0057* (2013.01); *A63B 21/00047* (2013.01); *A63B 21/4034* (2015.10); *A63B 23/0216* (2013.01); *A63B 23/0238* (2013.01); *A63B 23/03508* (2013.01); *A63B 23/03525* (2013.01); *A63B 23/0405* (2013.01); *A63B 23/0482* (2013.01); *A63B 23/10* (2013.01); *A63B 69/0059* (2013.01); *A63B 2022/0092* (2013.01); *A63B 2208/0204* (2013.01); *A63B 2208/0214* (2013.01); *A63B 2208/0228* (2013.01); *A63B 2208/0252* (2013.01); *A63B 2209/10* (2013.01); *A63B 2225/09* (2013.01); *A63B 2225/62* (2013.01)

(58) Field of Classification Search
CPC ..... A63B 21/4001; A63B 21/04; A63B 21/05; A63B 2208/0209; A63B 2208/0238; A63B 2208/0242; A63B 2208/0295; A63B 23/1236; A63B 23/08; A63B 21/4037; A63B 225/09
See application file for complete search history.

(56) References Cited

U.S. PATENT DOCUMENTS

| | | | | |
|---|---|---|---|---|
| 5,211,623 | A | * | 5/1993 | Sarkozi .................. A61F 5/055 128/DIG. 23 |
| 2014/0188024 | A1 | * | 7/2014 | Cox ......................... A61F 5/01 602/20 |

* cited by examiner

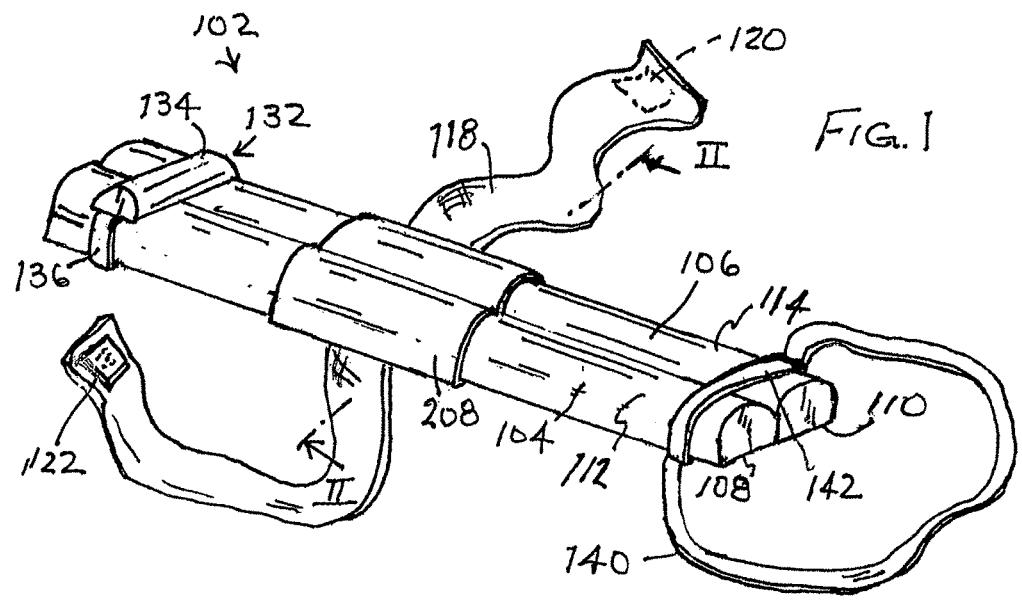
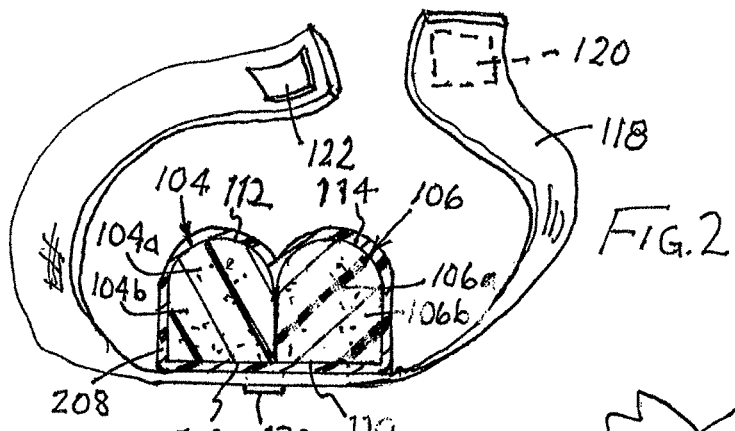
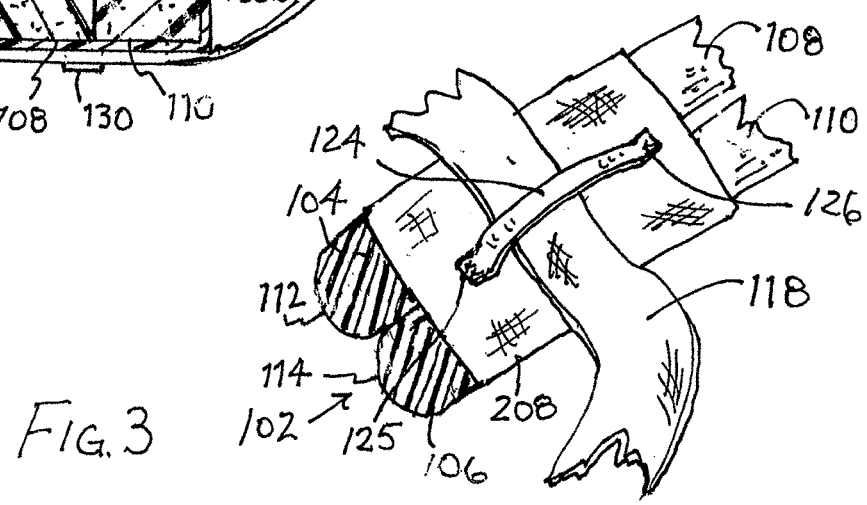

STABILIZATION ENHANCEMENT
EXERCISE DEVICE AND ASSOCIATED
METHOD

BACKGROUND OF THE INVENTION

This invention relates to a device for use in facilitating or assisting a user in enhancing skeleto-muscular stability control via exercise. This invention also relates to an associated exercise method utilizing the device.

Supine exercises on an unstable base challenge core stability. These exercises train torso, abdominal and hip muscles and increase stability of the pelvis and thus of the torso and spinal column.

OBJECTS OF THE INVENTION

An object of the present invention is to provide a device for use by an individual during supine exercises to enhance stability of the pelvis and spine.

An alternative or additional object of the present invention is to provide such a device that may be used by an individual during stability exercises while kneeling, seated or standing versions.

A related object of the present invention is to provide an improved supine exercise method.

These and other objects of the present invention will be apparent to one skilled in the art from the drawings and descriptions herein. Although every feature of the invention is attained in at least one embodiment of the invention, there is not necessarily any one embodiment that achieves all of the objects of the invention.

SUMMARY OF THE INVENTION

A device for facilitating or enhancing torso and pelvic stability exercises comprises two elongate semi-cylindrical resiliently compressible members so coupled to one another as to maintain a mutually parallel configuration, the resiliently compressible members each having a planar side and a cylindrically arcuate side, the planar sides being co-planar with one another. At least one and preferably several fastening or coupling elements are attached to the resiliently compressible members and configured for attachment to a user so that the resiliently compressible members are held against the user with either the planar sides or the arcuate sides in contact with the user in one use configuration and so that the other sides are in contact with the user in an alternate use configuration.

The fastening or coupling element preferably includes a strap or band extendable about a rib cage of the user. The strap or band is removable and can be reassociated with the compressible members so as to be utilizable in either mode of use.

A third resiliently compressible member may be attached to the two elongate semi-cylindrical resiliently compressible members at one end thereof so as to extend across the two elongate resiliently compressible members. The third resiliently compressible member is engageable by the user's head and is removable and repositionable so as to be adjacent either the arcuate sides or the planar sides of the two elongate resiliently compressible members.

The device may also include a foot entrainment element or brace such as a band or loop that is connectable to the compressible members at an end thereof opposite the head support. The foot brace may be engageable with the instep of one or both feet during an exercise or may include anklet straps (e.g., with VECRO fasteners) for coupling the foot brace to the user about one ankle for a single leg exercise or about both ankles when the legs are moved in tandem. The foot brace may be removably attached to the compressible members by a coupling band or strap that surrounds the compressible members and engages the same in a friction fit.

Thus, the head rest, the rib strap or band, and the foot brace are removably attached to the compressible members and may be adjusted in their respective positions relative to the compressible members. Any one or all of the head rest, the rib strap or band, and the foot brace may be removed from the compressible members and used separately.

A method for enhancing stability during supine exercises comprises, in accordance with the present invention, (a) providing a device including two elongate semi-cylindrical resiliently compressible members so coupled to one another as to maintain a mutually parallel configuration, the resiliently compressible members each having a planar side and a cylindrically arcuate side, the planar sides being co-planar with one another. The method further comprises (b) disposing the two elongate resiliently compressible members against a user's back, so that the resiliently compressible members are disposed in parallel to the user's spine and on opposite sides of the spine. In one mode of use of the device, the planar sides of the resiliently compressible members are against, or in contact with, the user's back, while the arcuate sides face away from the user and are in contact with a horizontal support surface such as a floor. In another mode of use, the arcuate sides of the resiliently compressible members are disposed in contact with the user, while the planar sides face away from the user (and in contact with an underlying support surface such as a floor). The method additionally comprises (c) attaching the resiliently compressible members to the user, (d) moving or elevating one of the user's legs preferably but not necessarily while maintaining the other leg in a supine and straight position (both legs may be moved in some exercise routines).

Other exercises utilizing the device of the present invention include variations of this basic exercise. For instance, one of the user's legs may be moved up and over the other leg while that other leg is maintained in a supine and straight position. In another exemplarily exercise, one leg is folded back and against the abdomen, to the extent possible, while the other leg is maintained straight and supine. In yet other exercises, both legs may be moved off of the horizontal support surface, which is typically a floor surface but may be a platform, stage, etc.

Where the device further includes a third resiliently compressible member (e.g., a head rest) extending across the two elongate resiliently compressible members at one end thereof, the method optionally includes placing a back side of the user's head against the third resiliently compressible member and resting the user's head against the third resiliently compressible member during the moving of the user's legs.

Where the planar surfaces are initially placed in contact with the user's back, the method may comprise disposing the two elongate resiliently compressible members against a user's back, so that the resiliently compressible members are disposed in parallel to the user's spine and on opposite sides of the spine and so that the arcuate sides of the resiliently compressible members are against the user's back, while the planar sides face away from the user. The user then executes one or more selected leg motion exercises. In that case, the third resiliently compressible member (the head rest) is preferably moved, if warranted, from a position adjacent the planar sides of the resiliently compressible members to a position adjacent the arcuate sides of the resiliently compressible members. In other words the head rest comes off to enable placement of the flat surfaces of the elongate compressible members on the horizontal support surface (floor, platform, etc.) while the head rest may be reattached to the device for use in the inverted configuration, where the arcuate surfaces are in contact with the user.

The attaching of the two resiliently compressible members to the user may be carried out by wrapping a band or strap about a torso of the user, the band or strap being attached to the exercise device, for instance, by being slipped under a locating band or strip which is attached at opposite ends to the two compressible members and extending in parallel thereto.

BRIEF DESCRIPTION OF THE DRAWING

FIG. 1 is a schematic top, front, and right side perspective view of a stability exercise assist or enhancement device in accordance with the present invention, for use in a supine posture.

FIG. 2 is a transverse cross-sectional view taken along plane II-II in FIG. 1.

FIG. 3 is a partial, broken away, rear, left side perspective view of the stability exercise assist or enhancement device of FIGS. 1 and 2.

DETAILED DESCRIPTION

Figure 4:
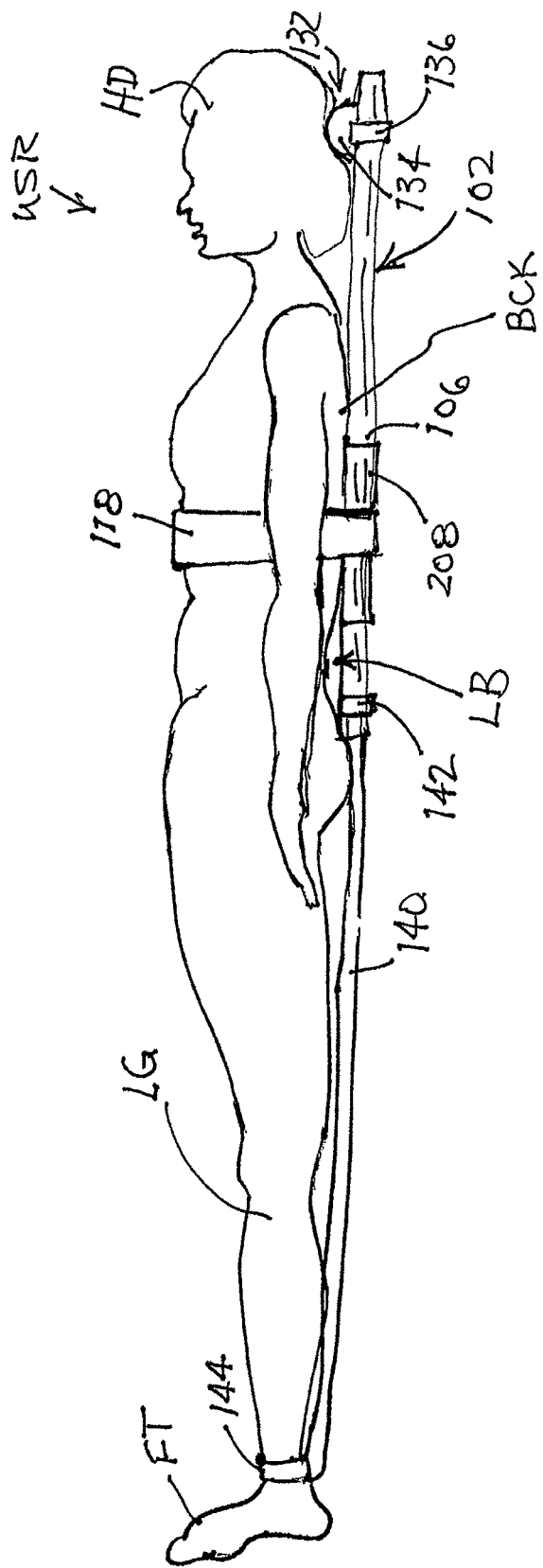
FIG. 4 is a schematic side elevational view showing use of the device of FIGS. 1-3 by a user.

FIG. 1 shows a device 102 particularly adapted for supine exercises that include moving one or both legs in order to improve the integrity of pelvic and torso muscle groups and enhance postural stability. Device 102 comprises two elongate resiliently compressible members 104 and 106 each approximately 40 inches in length. Each compressible member 104, 106 takes the form of a semi-cylinder 104a, 106a continuous with and sitting atop an elongate right rectangular prism 104b, 106b with a flat or planar side or surface 108, 110, and a cylindrically arcuate side or surface 112 or 114. Device 102 further comprises at least one coupling element 208 connected to compressible members 104 and 106. Coupling element 208 may take the form of a fabric band exemplarily made of neoprene that surrounds compressible members 104 and 106 at a central region thereof, preferably approximately aligned with a thoracic vertebral region of a user USR (FIG. 4) when resiliently compressible members 104 and 106 are disposed to extend from the head HD (FIG. 4) of the user USR to at least a lumbar region LB thereof. Coupling element 208 may be configured to conform to the arcuate outer surfaces 112, 114 and planar outer surfaces. 108, 110 of the resiliently compressible members 104, 106. In that case, coupling member may be sewn to itself along a seam (not shown) extending longitudinally between and parallel to resiliently compressible members 104 and 106. Coupling element 208 serves in part to maintain compressible members 104 and 106 in parallel relation to one another and at a maximum distance from one another. The maximum spacing is preferably no more than approximately ¼ inch (between the closest surfaces of the compressible members).

Compressible members 104 and 106 may be made of any closed cell or open cell polymeric foam material and are exemplarily made of a polymeric foam material such as polyethylene (PE) or EVA foam. Exercise assist device 102 further comprises a user attachment component in the form of a belt or strap 118 that may be provided with VELCRO type hook and loop fasteners 120 and 122 for securing the belt or strap tightly about a user's rib cage, preferably just south of the pectoral muscles or breasts. Rib belt or strap 118 is loosely and adjustably coupled to compressible members 104 and 106 via a strip 124 that is sewn or glued at its ends 125, 126 to coupling element or band 208 to form a passageway 130 traversed by belt or strap 118. Belt or strap 118 extends behind the user USR during use of the device. The longitudinal position of belt or strap 118 relative to compressible members 104 and 106 may be adjusted to suit individual users by sliding the belt orthogonally relative to strips 124 and 208, i.e., in a direction parallel to resiliently compressible members 104 and 106. Strip 124 has a length sufficient to accommodate users of all sizes.

In one mode of use, say, where the flat or planar sides 108 and 110 of compressible members 104 and 106 are disposed against the user and the arcuate sides 112 and 114 face away from the user, belt or strap 118 extends between the user USR and the compressible members 104 and 106 during use of the device 102. In another mode of use, where the flat or planar sides 108 and 110 of compressible members 104 and 106 face away from the user USR and the arcuate sides 112 and 114 are against the user, belt or strap 118 may surround both the user USR and the compressible members 104 and 106 during use of the device 102.

Exercise assist device 102 further comprises a head support/rest assembly 132 at one end of compressible member 104 and 106 for use as a head rest enabling or facilitating a user's pressing downward of the head HD (FIG. 4) to provide for spinal traction and stability building. Head support 132 includes a resiliently compressible member 134 attached to compressible members 104 and 106 via an elastic loop or band 136 which is preferably attached to compressible members 104 and 104 by friction owing to compressive forces exerted by loop or band 136. Compressible member 134 may be a segment of the same material and structure as compressible elements 104 and 106 and may be covered in neoprene or another stretchy "warming" fabric.

A method for enhancing stability during supine exercises uses device 102 by disposing the resiliently compressible members 104 and 106 against the user's back BCK (FIG. 4), so that the resiliently compressible members are disposed in parallel to the user's spine and on opposite sides of the spine and so that the planar sides 108, 110 of the resiliently compressible members, as well as coupling element or strip 208 are against or juxtaposed to the user's back BCK, while the arcuate sides 112, 114 face away from the user USR and engage the floor or other horizontal support surface. Resiliently compressible members 104 and 106 are attached to the user USR via strap or belt 118. In one typical exercise, the user USR moves a first leg LG up and over the other leg while that other leg is maintained in a supine and straight position (FIG. 4). Subsequently, in a mirror-image exercise, the user USR crosses the second leg over the first leg while that same leg is maintained in a supine and straight position.

Other supine exercises that improve stability using device 102 typically consist of moving one leg or both legs together. One leg or both may be elevated, with or without a bending at the knee(s). The motion of each leg may be entirely in a vertical plane or may include deviations laterally with respect to a vertical plane.

The use of device 102 enhances the use of various abdominal, back, pelvic, and leg muscles, improving coordination of and strengthening the muscles. With repeated use, pelvic and torso stability is enhanced, leading to improvements in posture and gait.

The user typically rests his or her head HD against the third resiliently compressible member 134 during the pertinent exercises, such as elevating and crossing over of the legs.

It is also possible to place the arcuate sides 112, 114 of the resiliently compressible members 104 and 106 against the user's back, while the planar sides 108, 110 face away from the user and contact the floor or other surface (via coupling strip 208 and optionally cover or casing 116). The third compressible member 134 is typically moved from one side of the device to the other during a conversion procedure, so that it is on the curved sides of members 104 and 106.

A user of stability building device 102 lies on rollers or compressible members 104, 106 and breathes into the rib wrap 118 while pressing the head HD against head rest 132 and pushing legs against an ankle restraint 140 in the form of a band or belt which may be attached to compressible members 104 and 106 at an end thereof opposite head rest 132 via an elastic or rubber band 142. The straightened leg pushes against the ankle restraint 140 as part of the exercise routine. Ankle restraint 140 may be provided at a region opposite rubber band 142 with an anklet loop 144, for instance, an elastic band or a belt having VELCRO-type fasteners (not shown). Alternatively ankle restraint 140 may be inserted along the soles of the feet FT, e.g., at an instep area (not designated).

It is to be noted that compressible members 104 and 106 may be molded as a unitary body, with rectangular prism portions 104b and 106b combined as one rectangular prismatic body. In another alternate embodiment described below with reference to FIGS. 5 and 6, the two compressible members 404 and 406 are joined, for instance, glued, to a planar plate 2080 that may be made of the same resilient material as compressible members 404 and 406.

Figure 5:
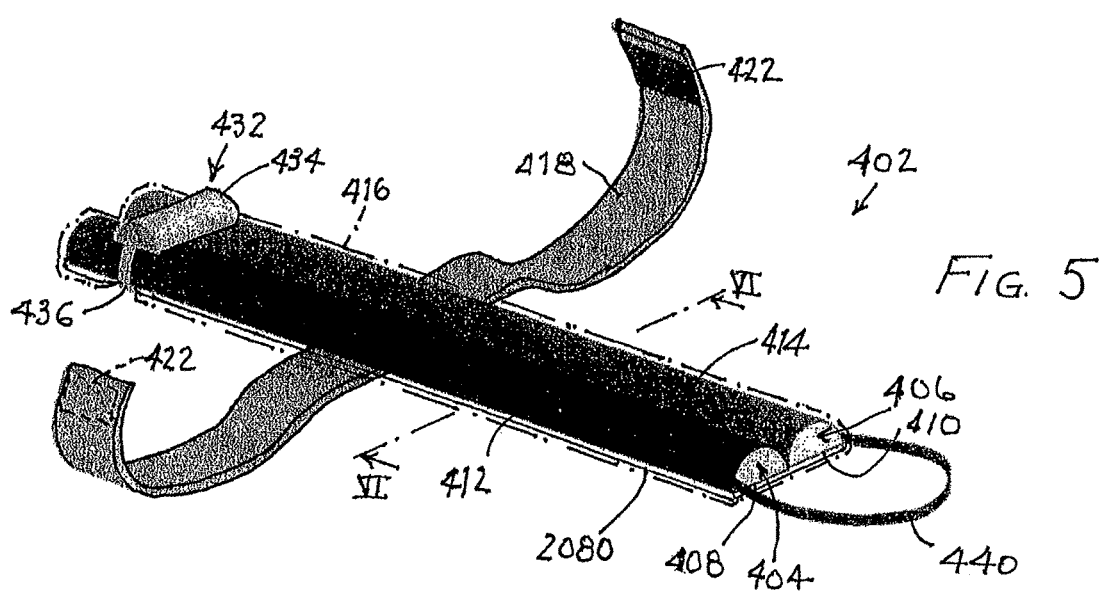
FIG. 5 is a schematic perspective view of another stability exercise assist or enhancement device in accordance with the present invention, for use in a supine posture.
Figure 6:
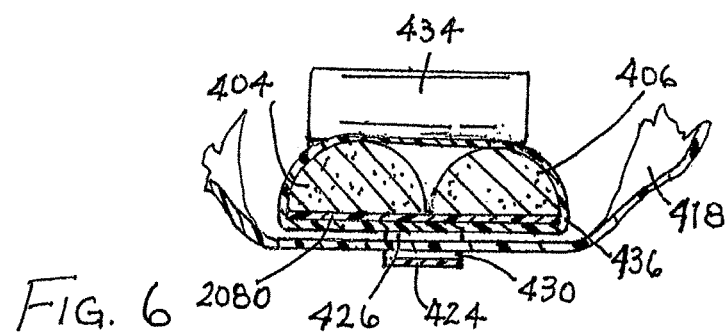
FIG. 6 is a transverse cross-sectional view taken along plane VI-VI in FIG. 5.

FIG. 5 shows a device 402 particularly adapted for supine exercises that include lifting one or both legs in order to improve the integrity of pelvic and torso muscle groups and enhance postural stability. Device 402 comprises two elongate resiliently compressible members 404 and 406 each approximately 40 inches in length. Each compressible member 404 and 406 takes the form of a semi-cylinder (or semi-cylinder with a rectangular prismatic base portion) with a flat or planar side or surface 408, 410, and a cylindrically arcuate side or surface 412 or 414. Device 402 further comprises at least one coupling element such as a planar fabric strip or plate 2080 connected to compressible members 404 and 406 along planar sides 408 and 410 thereof. Device 402 optionally includes a casing, envelope or cover 416 that contains compressible members 404 and 406 and that made be made of neoprene. If provided, casing, envelope or cover 416 assists coupling strip or plate 2080 in maintaining compressible members 404 and 406 in parallel relation to one another and at a maximum distance from one another. The maximum spacing is preferably no more than approximately ¼ inch (between the closest surfaces of the compressible members).

Compressible members 404 and 406 are preferably made of a polymeric foam material such as polyethylene (PE) or EVA foam. Exercise assist device 402 further comprises a user attachment component in the form of a belt or strap 418 that may be provided with VELCRO type hook and loop fasteners 420 and 422 for securing the belt or strap tightly about a user's rib cage, preferably just south of the pectoral muscles or breasts. Belt or strap 418 is loosely and adjustably coupled to compressible members 404 and 406 via a strip 424 that is sewn or glued at its ends 426 (only one end shown in FIG. 2) to coupling strip 2080 to form a passageway 430 traversed by belt or strap 418. Belt or strap 418 extends behind the user during use of the device. The longitudinal position of belt or strap 418 relative to compressible members 404 and 406 may be adjusted to suit individual users by sliding the belt orthogonally relative to strips 424 and 408. Strip 424 has a length sufficient to accommodate users of all sizes.

Exercise assist device 402 further comprises a head support/rest assembly 432 at one end of compressible member 404 and 406 for use as a head rest enabling or facilitating a user's pressing downward of the head to provide for spinal traction and stability building. Head support 432 includes a resiliently compressible member 434 attached to compressible members 404 and 406 via an elastic loop or band 436 which is preferably attached to compressible members 404 and 406 by friction owing to compressive forces exerted by loop or band 436. Compressible member 434 may be a segment of the same material as compressible elements 404 and 406 and covered in neoprene or another stretchy "warming" fabric.

The use of device 402 is essentially the same as the use of device 102 and provides the same benefits.

An ankle restraint 440 in the form of a band or belt may be attached to compressible members 404 and 406 at an end thereof opposite head rest 432. The straightened leg pushes against the ankle restraint 440 as part of the exercise routine.

Figure 7:
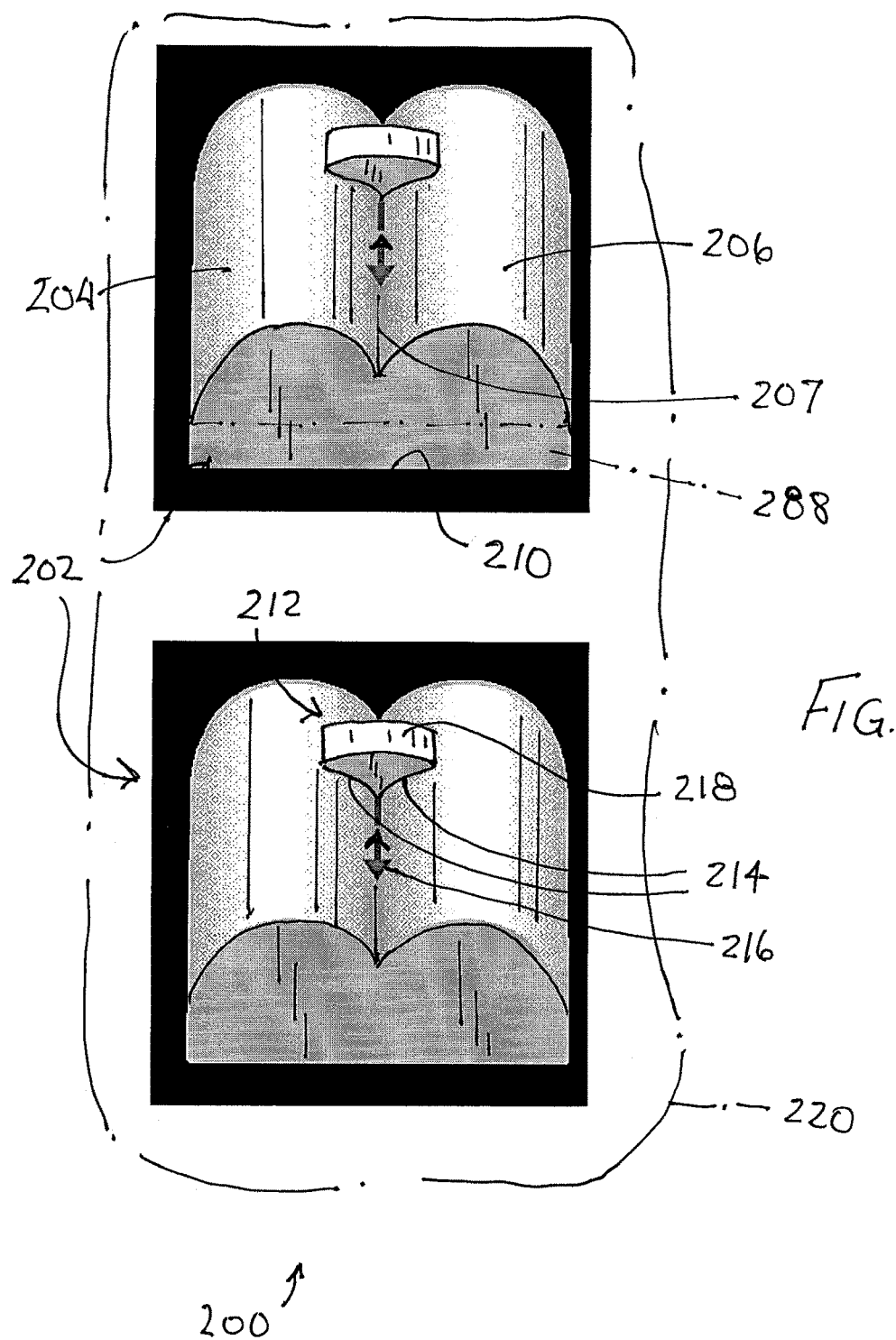
FIG. 7 is a schematic isometric view of a stability exercise assist or enhancement kit in accordance with the present invention, exemplarily but exclusively for use in a standing posture.

FIG. 7 shows a kit 200 including a pair of exercise assist or enhancement devices 202 particularly adapted for standing exercises that include partially or fully standing on one or both devices (see FIGS. 8-13) in order to improve the integrity of foot muscle groups and enhance flexibility, balance and stability within the feet. Devices 202 are 5-inch-square blocks of resiliently compressible material, 2.5 inches thick, including on one major side two semi-cylindrical profiles or parts 204 and 206 each approximately 5 inches in length. Semi-cylindrical profiles or parts 204 and 206 are contiguous with one another along a longitudinally extending center cleft 207. Preferably, semi-cylindrical profiles or parts 204 and 206 are seated atop an elongate right rectangular prism 288 with a flat or planar side or surface 210 opposite the semi-cylindrical profiles or parts 204 and 206. Kit 200 further comprises at least two wedges 212 each having a pair of concave undersurfaces 214 that engage outer surfaces (not separately designated) of semi-cylindrical profiles or parts 204 and 206 upon an insertion of the wedges into cleft 207 of exercise assist or enhancement device 202. As indicated by double headed arrows 216, wedges 212 are positionable at any point along the length of cleft 207. An upper surface 218 of each wedge 212 is preferably convex, e.g., in the form of a cylindrical sector.

Devices 202 including semi-cylindrical profiles or parts 204 and 206 may be made of any closed cell or open cell polymeric foam material and are exemplarily made of a polymeric foam material such as polyethylene (PE) or EVA foam. Devices 202 and wedges 212 may be provided in a pouch or carrying case 220.

Figure 8:
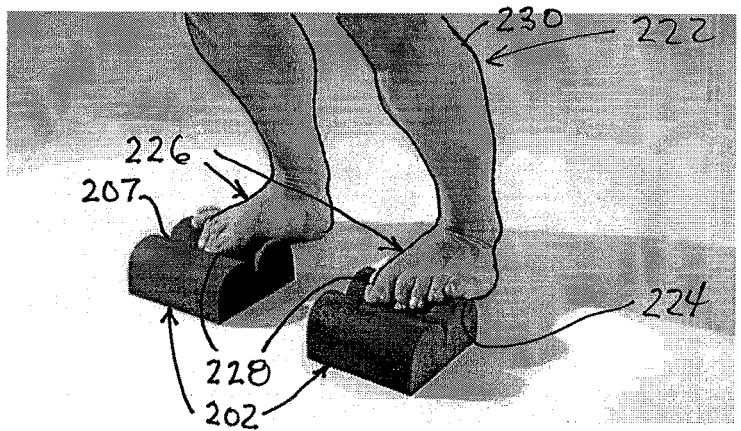
FIGS. 8-12 are respective partial perspective views showing exercises using a stability exercise assist or enhancement device included in the kit of FIG. 7.

In an exercise shown in FIG. 8, the user 222 places the balls 224 of the feet 226 on respective assist devices 202 so the toes 228 relax into the center channel or cleft 207. The user 222 attends to the feeling of the upper calf 230 lengthening as the user stands with knees straight. After a few seconds, the user 222 softens the knees to release the upper calf muscles 230. This exercise is preferably repeated for a minute daily, in order to avoid lower back and heel pain (plantar fascitis).

Figure 9:
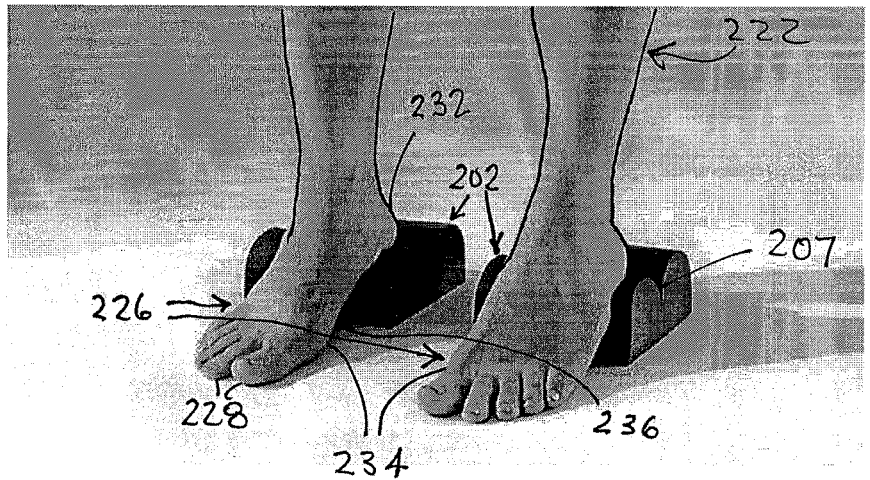

In an exercise depicted in FIG. 9, the user 222 places the backs of heels 232 at the center channel or cleft 207 and places the forefoot 234 on the floor. The user 222 tries to "dome" the arch 236 of the foot 226, imagining the heels 232 sliding towards the toes 228. This move will strengthen the toe flexors and foot intrinsics.

Figure 10:
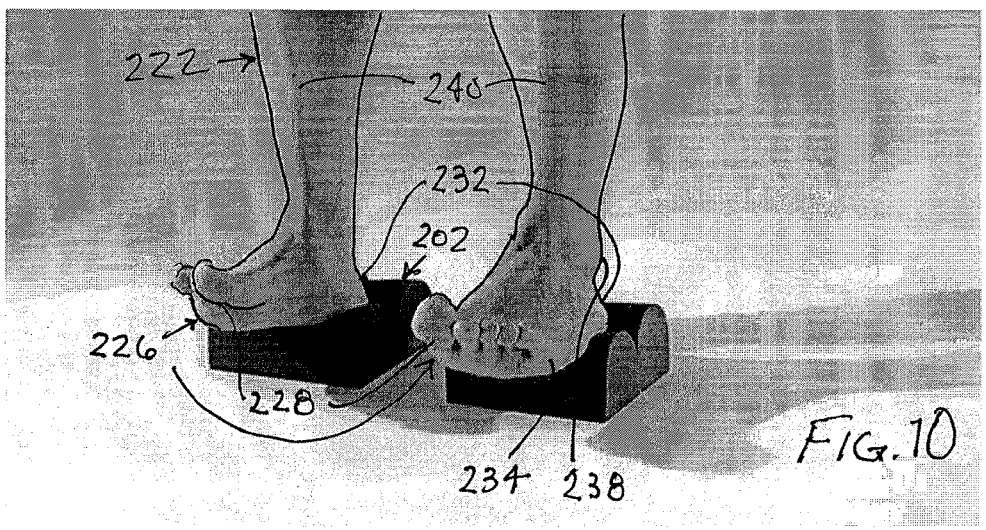

In an exercise illustrated in FIG. 10, with heels 232 on respective assist devices 202 and each forefoot 234 on the floor, the user 222 lifts the toes 228 first and then lifts the rest of the forefoot 234. This exercise awakens the tendons that cross the ankles 238. When the exercise is repeated quickly and the muscles of the ankle 238 and shin 240 will activate.

Figure 11:
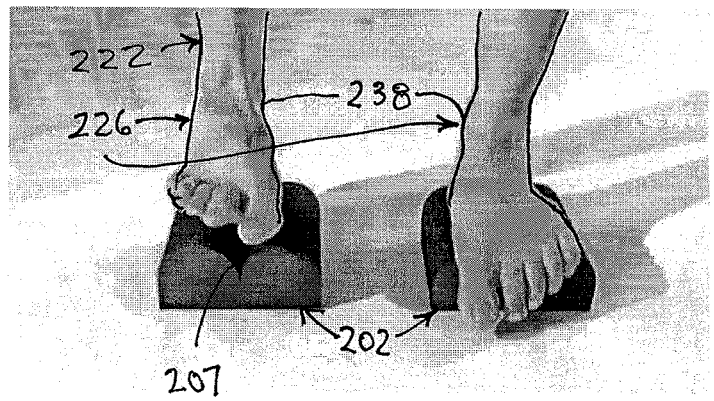

As shown in FIG. 11, in another exercise the user 222 turns assist device 202 so that center channel or cleft 207 faces the user. The user 222 inserts the wedges 212 (not visible in FIG. 11) into channels or clefts 207 slightly behind midpoints thereof. The user 222 then stands tall on wedges 212 so that the ankles 238 align with the front of the wedges 212. The user 222 will experience a realignment as the proprioceptors turn on.

Figure 12:
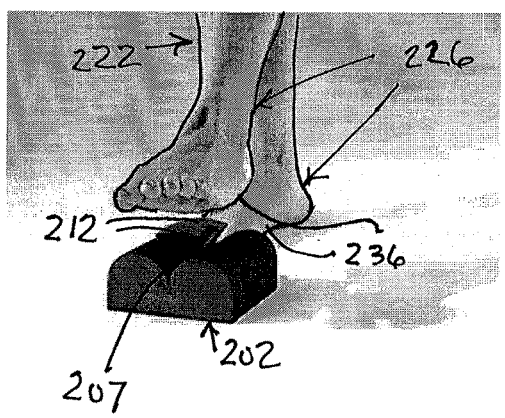

As illustrated in FIG. 12, in a related exercise the user 222 places both wedges 212 in the central channel or cleft 207 of one assist device 202 to support the arch 236 of the foot 226. The user 222 repeats the exercise of FIG. 11 with one foot 236 to increase the intensity and challenge. The user's body will vibrate. In this position, the user 222 can access the "true plumb line" that runs through the body.

Figure 13:
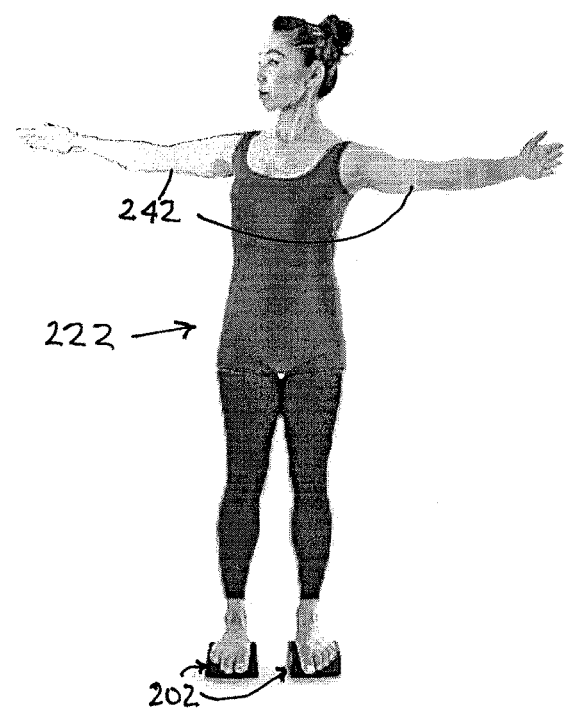
FIG. 13 is a perspective view of a person using, in another exercise, a stability exercise assist or enhancement device included in the kit of FIG. 7.

Per FIG. 13, the user 222 turns assist devices 202 over so flat sides or surfaces 210 (see FIG. 7) are facing upwardly. The user 222 stands on the upside-down assist devices 202 and practices balancing. During this exercise, the user 222 preferably touches a wall or chair for support. Gradually the user 222 raises his or her arms 242 to shoulder level as shown and attempts to balance. By standing on the assist devices 202 in this way the user 222 experiences micro movements throughout the body as it naturally finds a balance and center. The result is better posture and more graceful movement. When the user 222 steps off the assist devices 202, the user feels lighter and more buoyant immediately.

Although the invention has been described in terms of particular embodiments and applications, one of ordinary skill in the art, in light of this teaching, can generate additional embodiments and modifications without departing from the spirit of or exceeding the scope of the claimed invention. For instance, strap or band 118 may be replaced by any suitable form of a user attachment component that enables attachment of the device 102 to a user so that the elongate resiliently compressible members are maintained in substantial or approximate parallel relation to one another on opposite sides of the user's spine when the device is placed against the user's back and as the user engages in motion of the legs (and necessarily motion of the pelvis and lower back).

Head rest member 143 may be made of any suitable material or may take the alternate form, for instance, of an inflatable bladder or a stuffed pillow.

The compressible members 104 and 106 may be joined to one another by adhesive or heat bonding along the mutually contacting surfaces (not designated) of rectangular prismatic portions 104b and 106b. Alternatively or additionally, compressible members 104 and 106 may be joined by adhesive or heat bonding to a flat connector panel or sheet (compare coupling strip 2080) that is coextensive with the flat or planar surfaces 112 and 114 of the compressible members 104 and 106. In that case coupling member 208 may be omitted. Strip 124 may be attached directly (e.g., via glue or other bonding) to compressible members 104 and 106. Alternatively, strap or band 118 may be simply wrapped around both the user USR and the compressible members so as to attach the compressible members to the user.

In a modified structure, device 102 may be a unitary article like device 202. Thus, compressible members 104 and 106 are integrally formed with one another, geometric parts of the same block of resiliently compressible material.

For instance, the user can kneel on device 102, with one knee or two, optionally alternating from one leg to the other leg. Alternatively, the user may stand partially or fully on device 102 exactly as described herein above with reference to FIGS. 8-13. In another use, the user may sit on device 102, both buttocks on the device or one buttock and one thigh on the device and the other buttock and thick on the floor surface. In such exercises, the curved surfaces may face either upwardly or downwardly, whether the user is kneeling, sitting or standing.

Device 102 may be used in a standing posture, for instance, sandwiched between the user's back and a wall or architectural column. The curved surfaces or the device are held against the user's back as the user stands on his or her toes and balances or bends forward with a flat back.

As discussed above with reference to device 202, the user may stand on device 102 with different parts of the foot or feet. In the case of device 102 the user may alternatively walk along the length of the device, striding along the axial or longitudinal dimension of the device. Preferable the flat surface of device 102 faces upwardly in the walking exercise.

The miniature device 202 may be used on the head, the user walking around with the device balanced atop the head.

Accordingly, it is to be understood that the drawings and descriptions herein are proffered by way of example to facilitate comprehension of the invention and should not be construed to limit the scope thereof.

What is claimed is:
1. An exercise method comprising:
placing on a floor surface a plurality of exercise assist or enhancement devices each in the form of a square or prismatic block of resiliently compressible material, including on one major side two semi-cylindrical profiles or parts that are contiguous with one another and cooperate to define a longitudinally extending center cleft, with said semi-cylindrical profiles or parts facing upwardly;
placing the balls of a user's feet on respective ones of said exercise assist or enhancement devices so the toes of the user's feet relax into said center cleft of the respective ones of said exercise assist or enhancement devices;
standing with the user's knees straight after the placing of the balls of the user's feet on said respective ones of said exercise assist or enhancement devices; and
after a few seconds, softening the user's knees to release upper calf muscles.

* * * * *